United States Patent [19]
Hök

[11] Patent Number: 5,786,592
[45] Date of Patent: Jul. 28, 1998

[54] PULSE OXIMETRY SENSOR WITH FIBEROPTIC SIGNAL TRANSMISSION

[75] Inventor: Bertil Hök, Västerås, Sweden

[73] Assignee: Hök Instrument AB, Västerås, Sweden

[21] Appl. No.: 788,235

[22] Filed: Jan. 24, 1997

[51] Int. Cl.[6] .................................................. H01J 5/16
[52] U.S. Cl. ........................ 250/227.14; 250/227.18; 356/41; 128/633
[58] Field of Search .................. 250/227.14, 227.18, 250/227.2, 221, 205; 356/41; 128/633, 634, 637, 644, 667

[56] References Cited

U.S. PATENT DOCUMENTS 4,770,179  9/1988  New, Jr. et al. ..................... 128/633

*Primary Examiner*—Que Le
*Attorney, Agent, or Firm*—Walter D. Ames; Watson Cole Grindle Watson, P.L.L.C.

[57] ABSTRACT

A pulse oximetry sensor has a light emitting and light detecting part containing light emitting diodes and a photo detector electrically connected to a pulse oximetry instrument, and a two-halved clamp. An optical fiber cable is connected between the part and the clamp, and a power distributor transfers part of the available electric power from the pulse oximetry instrument to a power receiver supplying electric power to a signal amplifier.

10 Claims, 2 Drawing Sheets

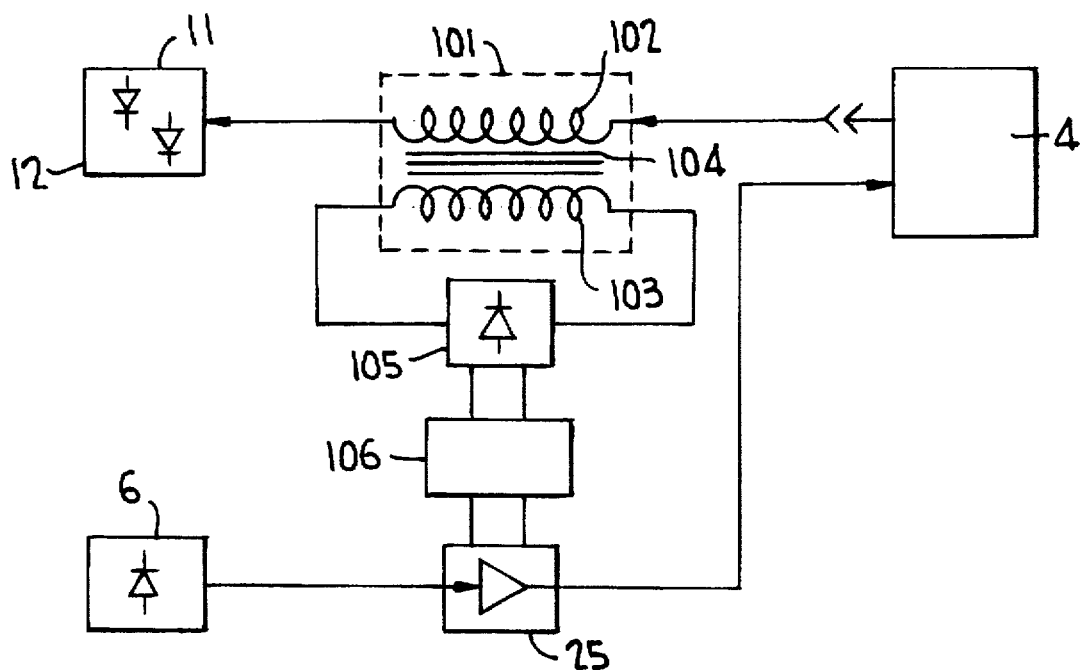
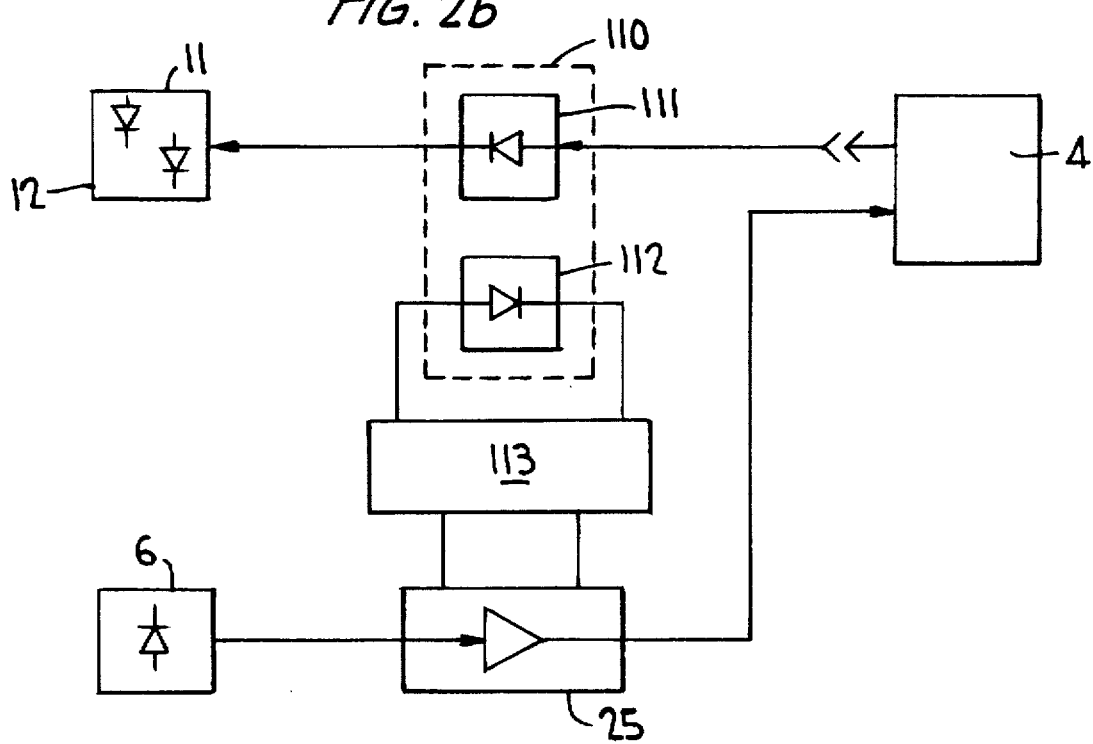

PULSE OXIMETRY SENSOR WITH FIBEROPTIC SIGNAL TRANSMISSION

FIELD OF THE INVENTION

The present invention relates generally to the monitoring of oxygen saturation of the arterial blood of a patient. More specifically, it relates to a non-invasive means for such monitoring, known as pulse oximetry.

BACKGROUND OF THE INVENTION

During critical health conditions it is important to provide continuous monitoring of the oxygen saturation of the arterial blood. This variable is available by a non-invasive measuring method, generally known as pulse oximetry and invented by T. Aoyagi, Japan, in 1974.

In its standard form, pulse oximetry is used in the following manner: Light is emitted from two light emitting diodes (LEDs) placed on one side of a finger clamp in two wavelength ranges, one in the red range at about 660 nm, and one in the near infrared around 940 nm. The signals from each of the wavelength ranges are detected by a photodiode at the opposing side of the finger clamp after trans-illumination through the finger, ear or another extremity. Separation of the signals from the two wavelength bands is performed by alternating the current drive to the respective light emitting diode, and by the use of time windows in the detector circuitry. Both the static signal, representing the intensity of the transmitted light through the finger and the signal synchronous to the heart beat, i.e., the signal component caused by the artery flow, is being monitored. Thus one has access to four measuring values, two from each wavelength band. By double ratioing of these four values, a numerical value is obtained which, at least approximately has an unambiguous relation with the oxygen saturation of the arterial blood.

Pulse oximetry is generally used throughout the world in anesthesia and intensive care for patient monitoring. Attempts have also been performed to use the method on certain occasions, e.g., during investigations using magnetic resonance imaging (MRI). Special demands on patient monitoring are then prevailing since it is sometimes necessary to put the patient to sleep, and direct observation is impossible due to the structure and size of the MRI equipment. Early attempts to use pulse oximeters in this environment have proved them to be unsuitable for the following reasons: Firstly, the MRI equipment can induce currents in the sensor cable which could, in worst cases, lead to burn injuries of the part of the body to which the sensor is applied. Secondly, the current drive to the light emitting diodes can cause interference on the images generated by the MRI equipment.

These problems are solved in the present invention by the fact that all signal communication between the patient and pulse oximeter instrument is performed optically by means of fiber optics. The invention is further being designed so that pulse oximeter instruments of standard type and design can be used. The fiberoptic sensor according to the invention can be connected in exactly the same way as an ordinary sensor without any adjustment or calibration procedures. This quality has great importance since measurement errors caused by errors of adjustment or calibration in the worst case could lead to erroneous treatment of the patient.

SUMMARY OF THE INVENTION

The present invention is comprised of a pulse oximetry sensor having an optical fiber cable connected between a light emitting/detecting part and a two-halved clamp including at least one power receiver supplying electric power to at least one signal amplifier.

In more detailed embodiments of my invention, the light emitting/detecting part contains at least one light emitting diode with emissions in the wavelength region of 650–670 nm. and at least one light emitting diode with an emission in the wavelength region of 920–960 nm.

The fiber optic cable may contain a multiplicity of optical fibers with maximal attenuation of 0.3 dB meter in the wavelength region of 650–960 nm. The cable may contain a multiplicity of fibers partitioned into two bundles so that a separate optical connection is obtained between each side of a two-halved clamp and the light emitting and light detecting parts.

According to other features of my invention, the light emitting and light detecting parts may be located within one box with an optical and electromagnetic shield interposed between those parts. Further, the cable and the two-halved clamp are preferably made from non-ferromagnetic material in their entireties. Also, the surfaces of the fiber endings may preferably be polished and brought into direct contact with polished surfaces of the light emitting diodes and photo diodes of the light emitting and detecting parts.

These and other objects, features and advantages of my invention will become more apparent when considered in connection with a detailed description of preferred embodiments of my invention, which are illustrated in the accompanying drawings.

DESCRIPTION OF THE DRAWINGS

FIG. 2(a) is a schematic circuit diagram illustrating one embodiment of power transfer means according to my invention, and FIG. 2(b) is a schematic circuit diagram illustrating another embodiment of such power transfer means.

DESCRIPTION OF PREFERRED EMBODIMENTS

Figure 1:
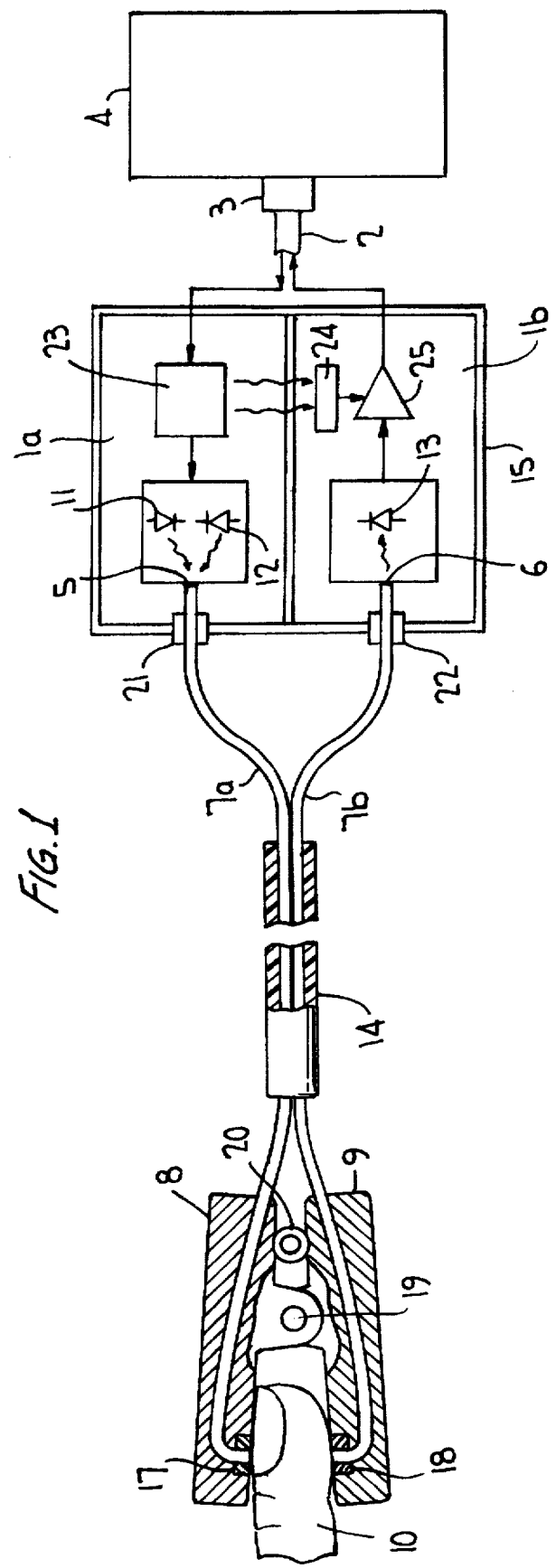
FIG. 1 is a partly schematic, partly perspective diagram of an optical probe in accordance with the present invention.

The achievement of exhangeability without adjustments or calibrations is partly a question of basic design and partly careful choice of materials and components which fulfill certain performance limits.

Below, the sensor according to the invention will be described in detail in relation to the enclosed FIG. 1, schematically depicting the design of the sensor. FIG. 2 shows detailed embodiments of a central function element of the sensor.

As shown in FIG. 1, the sensor according to the invention consists of two main parts, one of which is the light emitting and detecting part 1a and 1b, respectively, located within a box 15. The parts 1a and 1b are connected to the second part of the sensor, the fiber optic cable 7, and to a pulse oximetry instrument 4 via an electric cable 2 and a connector 3.

The fiber optic cable 7 is built up from a multitude of optical fibers running in parallel. These are partitioned in a way that a bundle 7a connects the light emitting part 1a with one side of a two-halved finger clamp 8, while its other side 9 is connected to the light detecting part 1b via the bundle 7b. Preferably, the bundles 7a, 7b are provided with separate mantles in a nontransparent material to ensure the optical isolation between the two sides.

The connection between the light emitting and the detecting parts 1a, 1b is provided by means of openings 21, 22 in the wall of the box 15. Preferably these openings are provided with identification marks. e.g., numerical or colour codings, and locks, e.g., snap locking so that connection and disconnection can be performed without the use of tools and without the risk of errors. Thus the fiberoptic cable 7, including the clamp 8,9 can be exchanged and replaced by a corresponding part having different size, depending on the patient's size, special requirements, or the like.

The ends of the optical fibers at the clamp 8, 9 are bent and positioned inside specially moulded parts 17, 18. These are designed to fit a finger 10, ear or other extremity to be inserted into the clamp 8, 9 and be trans-illuminated by the fiber endings attached directly against the skin surface. The light transmitted through the finger 10 is caught by the receiving fiber bundle in the moulded part 18 at the bottom side 9 of the clamp and is guided back to the light detecting part 1b via the fiber optic cable 7. Typically, the cable 7 contains 200–400 fibers with outer diameter 50–100 μm, with a common mantle 14 to protect from mechanical stress. The sides of the clamp are moveable along an axis through pivot 19. The attachment of the moulded parts 17, 18 is controlled by a spring 20, e.g., an elastic ring.

The light emitting part 1a contains a light emitting diode 11, emitting red light in the wavelength band 650–670 nm, and a light emitting diode 12 emitting infrared light in the wavelength band 920–960 nm. By grinding and polishing the package of the light emitting diodes and the optical fiber endings 5, and by close attachment between these surfaces, efficient transfer of light can take place to the optical fiber cable 7, while minimizing leakage of light to the ambient. The light emitting diodes are driven by current pulses generated according a known and standardized pattern from the pulse oximetry instrument 4 and transferred to the respective light emitting diode 11, 12 via electric leads in the cable connection 2. The current pulses are also passing a passive power distributor 23 which, in a non-galvanic way, is transferring a certain part of the pulse power to a power receiver 24, while most of the pulse power is passing over to the light emitting diodes 11, 12.

The light detecting part 1b contains a photo detector 13, e.g., a photo diode or a photo transistor which correspondingly with the light emitting diodes 11, 12 are in close physical contact with the fiber endings 6 to the part 7b of the fiber optic cable 7 which is transmitting the signal back from the finger 10. In the photo detector 13 weak current pulse are genereated synchronously with the transmitted light pulses from the light emitting diodes 11, 12. A significant power loss takes place in the fiber optic transmission if compared with a common pulse oximetery sensor, in which the photo diode is attached directly against the skin. In order for a standard pulse oximetry instrument to be able to detect these weaker signals, it is necessary to amplify them in the signal amplifier 25, which is powered from the power receiver 24. The outlet of the signal amplifier 25 is electrically connected via the cable 2 and the connector 3 to the pulse oximetry instrument 4, where further amplification, filtering, signal processing and information presentation is performed.

The light emitting and light detecting parts 1a and 1b are mutually shielded both optically and electromagnetically with a screen 16. The optical isolation between the two sides should be at least 60 dB. The electromagnetic shield is further extending over the the cable 2 by a separate shielding mantle over detector leads and current carrying leads to the light emitting diodes 11, 12 (not depicted in FIG. 1, function and design should be obvious).

The power transfer via the power distributor 23 and the receiver 24 can be performed using several embodiments, two of which are shown in FIG. 2. FIG. 2a) shows a solution built up by a pulse transformer 101 with a primary winding 102 connected in series in the current drive lead between the pulse oximetry instrument 4 and the light emitting diodes 11, 12. The secondary winding 103 of the pulse transformer is connected to a diode bridge 105 which performs rectification of the voltage induced in the secondary coil 103. The primary winding 102 thus corresponds to the power distributor 23 of FIG. 1, while the secondary winding 103 corresponds to the power receiver 24. Furthermore, there is a voltage controller 106 connected. The output voltage from this is a stable DC voltage with insignificant fluctuations. This voltage provides power to the signal amplifier 25 which amplifies the weak current pulses generated by the photo detector 6, and transfers the amplified signal to the pulse oximetry instrument 4. The pulse transformer 101 is thus transferring power from the light emitting part of the sensor to its detecting part without galvanic contact. The efficiency of theis transfer is high, especially if a ferrite core 104, e.g., of toroid type, is used between the primary and secondary windings 102, 103.

FIG. 2b) shows a solution built up with an optocoupler 110 with a light emitting diode 111 connected in series in the current drive lead between the pulse oximetry instrument 4 and the light emitting diodes 11, 12. The receiver side of the optocoupler 110 consists of one or several photo diodes or solar cells 112 generating a voltage upon illumination. In this case the light emitting diode 111 is a power didtributor 23 according to FIG. 1, while the photodiodes or solar cells 112 are power receivers 24. Furthermore, there is a voltage controller 113 connected, the voltage from this is a stable DC voltage with insignificant fluctuations. This voltage is powering the signal amplifier 25, amplifying the weak current pulses and transferring them to the pulse oximetry instrument 4. The optocoupler 110 is thus transferring electric power from the light emitting part of the sensor to its detecting part without galvanic contact.

Typical values of available pulse power from the pulse oximetry instrument via the cable connection 4 is 100–500 mW. To drive the signal amplifier 25 a maximum of 10 mW is required. Besides the described transfer principles of FIGS. 2a) and b), it is possible to use thermal, mechanical, pneumatic, hydraulic and acoustic principles within the framework of the present invention.

The requirements mentioned in the introduction that the sensor according to the invention should allow exchangeability against pulse oximetry instruments of different serial numbers, type numbers, models and producer etc generate implications both regarding the design as described above, and also in terms of performance of the included elements. For example, the wavelenght bands of the light emitting diodes 11, 12 should be carefully specified. Their emittance should also be optimized. For the red LED a lower limit of 3 candela at maximally allowed current is valid, for the infrared diode there is a lower limit of 20 MW per steradian. Furthermore, the spectral sensitivity of the photo diode should not vary more than a factor of 2 over the wavelength interval 650–960 nm, and the noise level should not exceed 2 fW/(Hz)½ (noise level is denoted in equivalent optical power, divided by the square root of the bandwidth in periods per second, Hz). The fiberoptic cable should not attenuate more than 0.3 dB in this wavelength range, since the transmission distance often exceeds 10 meters. This implicates that only inorganic materials, for example highly purified glass or silica can be used in the light-guiding core of the optical fibers. Another important characteristicsis that no materials of the fiberoptic cable 7 or the clamp 8, 9 may be ferromagnetic, since this would distort the MR images.

The invention is characterized by the enclosed claims. A large number of detailed embodiments are possible within the framework of these claims and the standpoint of technology.

I claim:

1. Pulse oximetry sensor with fiber optic signal transmission comprising:

a light emitting and light detecting part (1a, 1b) containing light emitting diodes (11, 12) with emission in at least two wavelength regions and at least a photo detector (13) with electric connection (2) via one or several connectors (3) to a pulse oximetry instrument (4), in which said light emitting diodes (11, 12) and photo detector (13) are optically connected to one end of at least one fiber optic cable (7) to the other end of which is connected to a two-halved clamp (8, 9) for fixation and transillumination of a finger, an extremity or other transilluminable body organ, and at least one power distributor (23) transferring a part of the available electric power from said pulse oximetry instrument (4) via said electric connection (2) to at least one power receiver (24), supplying at least one signal amplifier (25) with electric power.

2. Sensor according to claim 1, wherein said light emitting and detecting parts (1a, 1b) are individually exchangeable against said fiber optic cable (7), inclusive said two-halved clamp (8, 9) and vice versa without adjustment or calibration.

3. Sensor according to claim 1, wherein said light emitting and detecting parts (1a, 1b) contain at least a first light emitting diode (11) with emission in the wavelength region 650–670 nm with an emittance exceeding 2 candela, at least a second light emitting diode (12) with emission in the wavelength region 920–960 nm and emittance exceeding 20 mW/steradian and at least one photo detector (13) the sensitivity of which varies less than a factor of within and between said wavelength regions and with an equivalent noise power less than 2 fW/(Hz)½.

4. Sensor according to claim 1, wherein said fiber optic cable (7) contains a multitude of optical fibers with maximal attenuation of 0.3 dB/meter in the wavelength region 650–960 nm.

5. Sensor according to claim 1, wherein said fiber optic cable (7) contains a multitude of optical fibers partitioned into two bundles (7a, 7b) so that separate optical connection is obtained between each side of said two-halved clamp (8, 9) and the light emitting (1a) and light detecting (1b) parts, respectively, having an optical isolation between said sides of the clamp exceeding 60 dB.

6. Sensor according to claim 1, wherein said fiber optic cable (7) has a common mantle (14).

7. Sensor according to claim 1, wherein said light emitting and light detecting parts (1a, 1b) are located within one box (15) with optical and electromagnetic shield (16) between said light emitting and detecting parts (1a, 1b).

8. Sensor according to claim 1, wherein two-halved clamp (8, 9) contains two moulded parts (17, 18) with optical fiber connection with bends for the direction of propagation of the light, a pivot (19) for turning movements along one axis and an elastic spring (20) for fixation against said extremity (10).

9. Sensor according to claim 1, wherein said fiber optic cable (7), inclusive of said clamp (8, 9) is completely made from non-ferromagnetic materials.

10. Sensor according to claim 1, wherein the surfaces of said fiber endings (5, 6) are polished and can be brought into direct contact with polished surfaces of said light emitting diodes (11, 12) and photo diode of said light emitting and detecting parts (1a, 1b).

* * * * *